United States Patent [19]

Ivanov et al.

[11] Patent Number: 4,678,853
[45] Date of Patent: Jul. 7, 1987

[54] 1-(3,4-DIMETHYLBENZYL)-2-(N-ALKYL)-CARBAMOYL TETRAHYDROISO QUINOLINES

[75] Inventors: Chavdar B. Ivanov; Donka M. Mondeshka; Nikolina D. Berova; Rossitza S. Rakovska; Yordanka T. Panova; Marko T. Markov; Radi G. Ovcharov; Petko D. Usunov; Orhideya B. Zabunova, all of Sofia, Bulgaria

[73] Assignee: T P O "Pharmachim", Sofia, Bulgaria

[21] Appl. No.: 818,489

[22] Filed: Jan. 13, 1986

[51] Int. Cl.$^4$ ............................................. C07D 217/06
[52] U.S. Cl. .................................................... 546/146
[58] Field of Search ........................................ 546/146

[56] References Cited

U.S. PATENT DOCUMENTS

| | | |
|---|---|---|
| 3,725,388 | 4/1973 | Grell et al. ............................ 546/146 |
| 3,875,167 | 4/1975 | Kupchan et al. ..................... 546/146 |
| 3,905,982 | 9/1975 | Yonan .................................. 546/146 |

Primary Examiner—Glennon H. Hollrah
Assistant Examiner—James H. Turnipseed
Attorney, Agent, or Firm—Karl F. Ross; Herbert Dubno

[57] ABSTRACT

Compounds of the Formula (I)

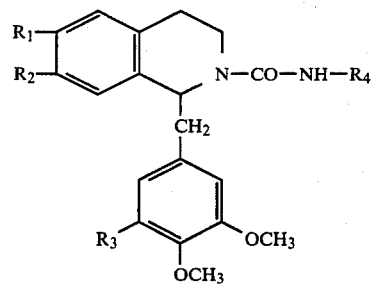

wherein $R_1$ and $R_2$ are hydroxyl or methoxyl; $R_3$ is hydrogen or methoxyl; and $R_4$ is methyl or chloroethyl; are disclosed having the ability to inhibit adenylatecyclase.

4 Claims, 1 Drawing Figure

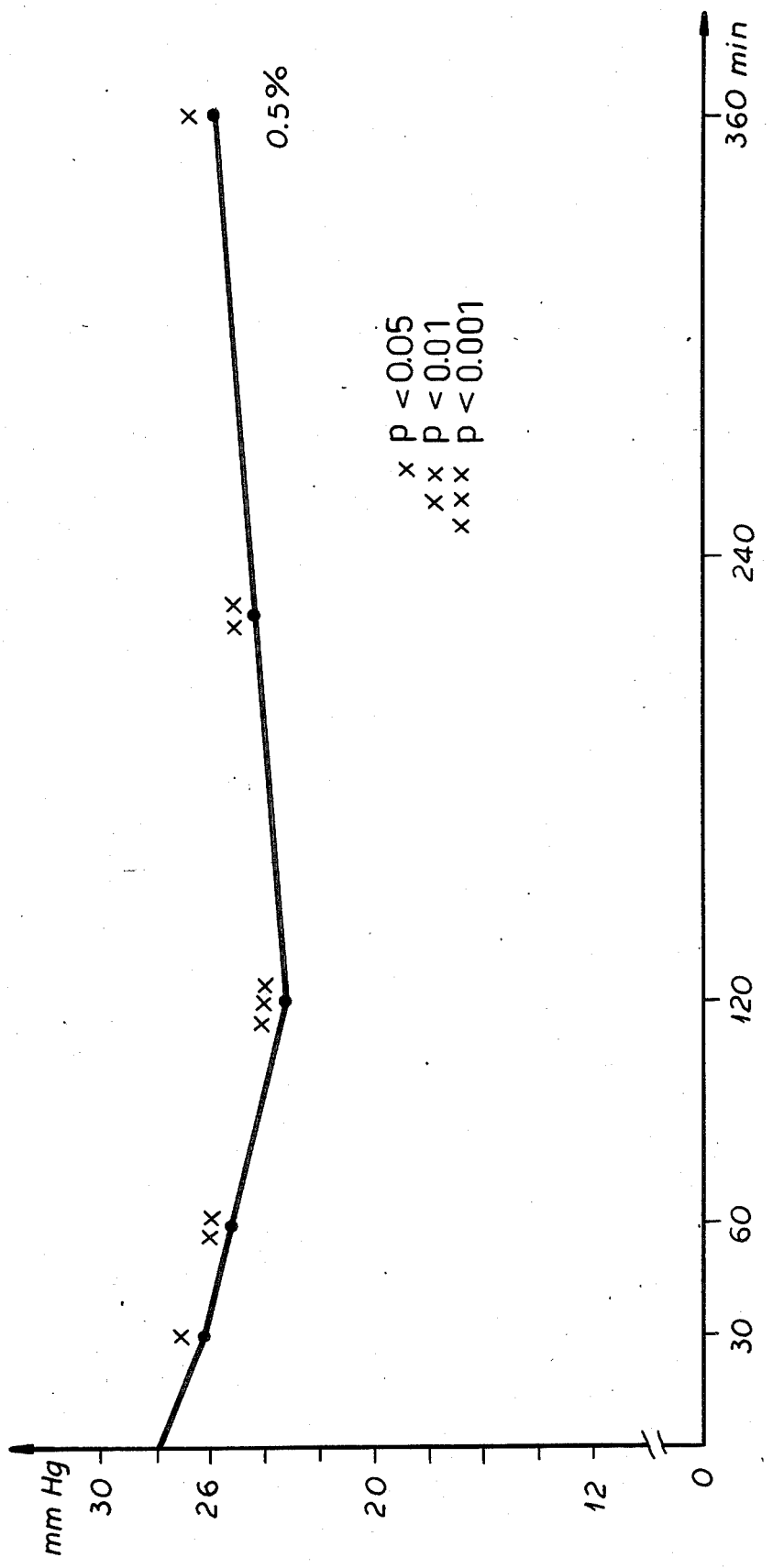

1-(3,4-DIMETHYLBENZYL)-2-(N-ALKYL)-CARBAMOYL TETRAHYDROISO QUINOLINES

FIELD OF THE INVENTION

This invention refers to 1-benzyl-2-(N-substituted)-carbamoyl-tetrahydroisoquinolines which are inhibitors of beta-adenylatecyclase and a method for preparation thereof.

BACKGROUND OF THE INVENTION

It is known that beta-adenylatecyclase is the cause of production of intraocular liquid and that inhibitors of this enzyme can be potential antiglaucoma agents.

1-benzyl- or phenyl-N(dialkyl-aminoalkyl)-carbamoyltetrahydroisoquinolines with antiarrhythmic and bactericidal activity are known and 1-benzyl-N-alkyl-carbamoyl-tetrahydroisoquinolines with antiepileptic activity.

OBJECT OF THE INVENTION

The object of the invention is to synthesize new 1-benzyl-2-(N-substituted)-carbamoyl-tetrahydroisoquinoles which are inhibitors of adenylatecyclase and to provide a method for preparing them.

DESCRIPTION OF THE INVENTION

According to the invention there are synthesized 1-benzyl-2-(N-substituted)-carbamoyl-tetrahydroisoquinolines with formula:

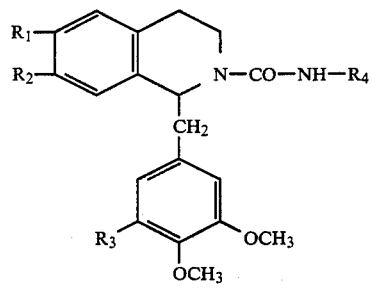

I in which $R_1$ and $R_2$ are hydroxyl or methoxyl groups, $R_3$ is hydrogen or a methoxyl group, $R_4$ is a methyl or chloroethyl group.

1-benzyl-2-(N-substituted)-carbamoyl-tetrahydroisoquinolines with formula I are prepared according to the invention by interaction of equimolar quantities of 1-benzyl-tetrahydroisoquinolines with formula II and aliphatic isocyanates with formula III by the following reaction scheme:

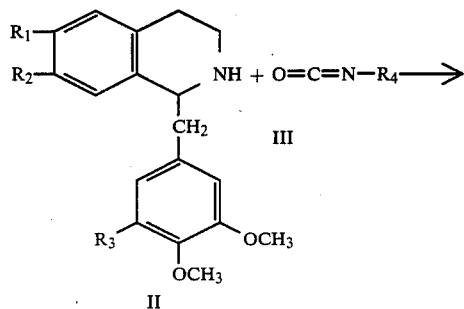

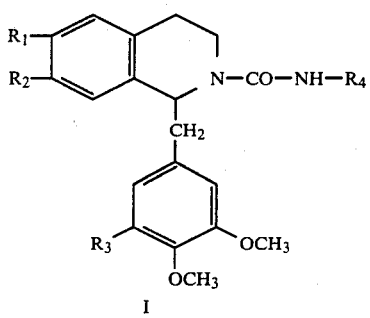

I in which $R_1$ to $R_4$ have the meanings given hereinabove.

The reaction takes place in a medium of chlorinated hydrocarbons (chloroform, tetrachlormethane, dichlormethane, methylenechloride), aromatic hydrocarbons (benzene, toluene) or aliphatic ketones (acetone, methylethylketone), in particular chloroform and acetone, in a temperature range from 20° C. to the temperature of boiling of the organic solvent.

The initial tetrahydroisoquinolines of formula II are prepared according to known methods as described in the prior art.

The isolation of carbamoyl derivatives of formula I is achieved by filtration of the crystals formed during the reaction or by distillation of the organic solvent under vacuum. In order to remove the contaminations of the initial tetrahydroisoquinoline, the raw-product is treated by diluted hydrochloric acid and then recrystalized from a suitable organic solvent as for example aliphatic alcohol (methanol, ethanol, isopropanol), aliphatic ketone (acetone) or ester of organic acids (ethylacetate).

As aliphatic isocyanates can be used methylisocyanate and 2-chlorethylisocyanate.

BRIEF DESCRIPTION OF THE DRAWING

The sole FIGURE in this case is a graph in which the influence of the Compound (1a) on intraocular pressure of rabbits is plotted against time.

SPECIFIC DESCRIPTION

The structure of the compounds prepared in accordance with the invention is confirmed by data of elemental analysis and IR and NMR-spectroscopy.

1-benzyl-2-(N-substituted)-carbamoyl-tetrahydroisoquinolines with formula I possess an inhibiting effect with respect to beta-adenylatecyclase in rat brain and lung. This effect is expressed the most distinctly in the case of S-(+)-1-(3,4,5-trimethoxybenzyl)-2-(N-[2-chlorethyl]-carbamoyl)-6,7-dihydroxy-1,2,3,4-tetrahydroisoquinoline of the formula Ia which surpasses in its activity the known adenylatecyclase inhibitors from the group of the phenothiazines, buterophenones or propanol. The results from the biochemical study of the compound of the formula 1a are given in a table on the following page. It is seen that the tetrahydroisoquinoline derivative Ia causes a well expressed and statically significant decrease of the intraocular pressure of non-narcotisized rabbits in local administration in form of 0.5% solution. The effect appears already in the 30$^{th}$ minute, with a maximum in the 120$^{th}$ minute and it is long lasting while not returning to the initial level in the checked 6 hours period (see the drawing).

TABLE

Inhibiting of beta-adenylatecyclase by S—(+)-1-(3,4,5, trimethoxybenzyl)-2-(N—[2-chlorethyl]-carbamoyl)-6,7-dihydroxy-1,2,3,4 tetrahydroisoquinoline Ia

| Tissue<br>1 | Ia(molar conc.)<br>2 | Adenylatecyclase activity<br>M/mg/min<br>3 |
|---|---|---|
| Brain | — | 284 + 66 |
| Brain | $1.10^{-5}$ | 26 + 7 |
| Brain | $1.10^{-6}$ | 73 + 12 |
| Brain | $1.10^{-7}$ | 104 + 23 |
| Lung | $1.10^{-5}$ | 11 + 3 |
| Lung | $1.10^{-6}$ | 28 + 11 |
| Lung | $1.10^{-7}$ | 66 + 21 |
| Lung | — | 188 + 36 |

The invention is illustrated and better explained by the following examples:

EXAMPLE 1

Preparation of s-(+)-1-(3,4,5 trimethoxybenzyl)-6,7-dihydroxy-2-(N-[2-chlorethyl]-carbamoyl)-1,2,3,4-tetrahydroisoquinoline Ia.

3,3 g of s-(−)-1-(3,4,5 trimethoxybenzyl)-6,7-dihydroxy-1,2,3,4-tetrahydroisoquinoline are suspended in 66 ml dry chloroform, then is added 0.7 ml 2-chloroethylisocyanate and the reaction mixture is stirred at ambient temperature for 24 hours and 15 minutes. After adding the isocyanate, the initial product passes in solution and after one hour begins the formation of crystals from the carbamoyl derivative. At the end of the reaction period the crystal precipitate is filtered, then washed with chloroform and suspended in 120 ml 5%-hydrochloric acid solution while stirring continuously for 30 min. Thereafter the precipitate is filtered. This operation is repeated five times. The thus treated product is washed with water to neutral reaction and is dried at a temperature of 60° C. There is obtained an amount of 2.9 g compound Ia which is recrystallized from ethylacetate-methanol. The crystallization is carried out at ambient temperature for 24 hours. The crystals obtained are filtered, washed with ethyl-acetate and dried at 60° C. Thus are obtained 1.3 g of compound Ia with melting point 152°–154° C. and $(alpha)_D^{22} = +39.13$/methanol, $c=0.55$/.

| Elemental analysis: for $C_{22}H_{27}N_2O_6Cl$ | | | | |
|---|---|---|---|---|
| | C | H | N | Cl |
| Calculated, %: | 58.60 | 6.03 | 6.21 | 7.86 |
| Found, %: | 58.20 | 6.10 | 6.42 | 7.56 |

NMR-spectrum/DMSO-$d_6$ M.F.: 2.60–3.85/m, 8H/methylene protons in isoquinoline nucleus and for N—$CH_2$—$CH_2$—Cl/3.40: /d 2H, y=6 Hz/ —$A^r$ —$CH_2$, 3.53/S, 3H/, 3.62/S, 6H/ —$CH_3O$, 5,0.5/t, 1H; y=6 Hz/ for $H_1$, 6.26/S, 2H/, 6.37/S, 1H/, 6.45/S, 1H/-four aromatic protons, 8.48/S, 1H/ and 8.59/S, 1H/ —OH groups.

EXAMPLE 2

Preparation of S(+)-1-(3,4,5 trimethoxybenzyl)-2-(N-methyl-carbamoyl)-6,7-dihydroxy-1,2,3,4-tetrahydroisoquinoline-compound 1b.

One gram S-(−)-1-(3,4,5-trimethoxybenzyl)-2-(N-methylcarbamoyl)-6,7-dihydroxy-1,2,3,4-tetrahydroisoquinoline is suspended in 40 ml acetone, then is added 0.16 ml methylisocyanate and the reaction mixture is boiled for 10 hours. After staying one night, the crystals thus formed are filtered, washed with acetone and dried at 60° C. After recrystallizing two times from acetone-methanol are obtained 0.3 g. of compound 1b with melting point 195°–196° C./$alpha/_D^{22} = +34.18$-/MeOH, $c=0.55$/.

| Elemental analysis for $C_{21}H_{26}O_6N_2$ | | | |
|---|---|---|---|
| | C | H | N |
| Calculated, %: | 62.68 | 6.50 | 6.96 |
| Found, %: | 62.38 | 6.80 | 6.56 |

Infrared/nujol/$cm^{-1}$ 1690, 3420

NMR/DMSO—$d_6$ ppm: 2.40/q, 3H, y=Hz/ —$CH_3NH$: 2.36–2.54: m, 4H/ for methylene protons with $C_3$ and $C_4$: 3.22/q, 2H, y+6.5 Hz/ —$A^r$—$CH_2$, 3.50/S, 3H/ and 3.58/S, 6H/ for three $CH_3O$; 5.02/t, 1H, y=6.5 Hz: for proton with $C_1$; 5.96/q, 1H, y=4 Hz/ —CONH, 6.22/S, 2H/; 6.29/S, 1H/; 6.35/S, 1H/-aromatic protons; 8.32/S, 1H and 8.45/S, 1H/—OH groups.

EXAMPLE 3

Preparation of 1-(3,4-dimethoxybenzyl)-2-(N-[2-chlorethyl]-carbamoyl)-6,7-dimethoxy-1,2,3,4-tetrahydroisoquinoline 1c 2.86 g of tetrahydropapaverine are dissolved in 15 ml chloroform, then are added 0.7 ml of chlorethylisocyanate and the reaction mixture is stirred at ambient temmperature for 24 hours. The chloroform is distilled to dryness under vacuum. The thus obtained oily residue is suspended in ether and is left there to stay at a temperature about 0° C. for two days. A solid amorphous product is obtained that is filtered, washed several times with ether and dried at ambient temperature. Thus is prepared 1 g of compound 1c with melting point 73°–76° C.

| Elemental analysis for $C_{23}H_{28}N_2O_5Cl$ | | | | |
|---|---|---|---|---|
| | C | H | N | Cl |
| Calculated, %: | 61.67 | 6.29 | 6.25 | 7.91 |
| Found, %: | 61.91 | 6.35 | 6.52 | 8.10 |

IR/nujol/$cm^{-1}$: 1650, 3340

NMR/$CDCl_3$/ppm: 2.60–4.24 and 4.38–4.60/m, 8H/ for methylene protons with $C_3$ and $C_4$ and for methylene protons from N—$CH_2$—$CH_2$—Cl; 2.96/q, 2H, y=6.5 Hz/—Ar—$CH_2$; 4.95/t, 1H, y=6.5 Hz/ for proton with $C_1$; 3.82/S, 6H/ and 3.96/S, 6H/ for four $CH_3O$; 6.00/t, 1H, y=4.5 Hz/—CO—NH; 6.18-7.20/m, 5H/ for aromatic protons.

EXAMPLE 4

Influence of (+)-1-(3,4,5 trimethoxybenzyl)-2-(N-[2-chlorethyl]-carbamoyl)-6,7-dihydroxy-1,2,3,4-tetrahydroisoquinoline Ia on adenylatecyclase activity in brain and lung of rats.

The enzyme activity is determined in homogenates of brain and lung prepared in a ratio 1:10/tissue:buffer, Tris -HCl, pH=7.4, 0.1M/. Use is made of the radioisotope method of Krishna, Weiss and Brodi. The standard incubation samples contain in a final volume of 100 mkl the following components: buffer 0.1 $\mu S^3$ H-adenosintriphosphate in concentration $1.10^{-3}M$, theophylline $1.10^{-3}M$ and 3,5-adenosinemonophosphate in concentration $5.10^{-4}M$. The operational samples contain in addition the compound Ia suspended in Tween. The samples are incubated during 10 min. The new formed labeled 3,5-adenosinemonophosphate is isolated in columns with neutral alumina, it is mixed with scintillation liquid and then counted by means of a scintillation spectrometer.

EXAMPLE 5

Influence of (+)-1-(3,4,5 trimethoxybenzyl)-2-(N-[2-chlorethyl]-carbamoyl)-6,7-dihydroxy-1,2,3,4-tetrahydroisoquinoline Ia on ophthalmotone on non-narcotisized rabbits in local administration (two drops in the eye) in form of 0.5% solution.

The intraocular pressure is measured by means of the tonemeter of Schiotz before and on the 30, 60, 120, 240 and 360 min after administering compound Ia. The data obtained are calculated in mm Hg according to the table of Leydhecker.

What is claimed is:

1. 1-benzyl-2-(N-substituted)-carbamoyl-tetrahydroisoquinoline of formula:

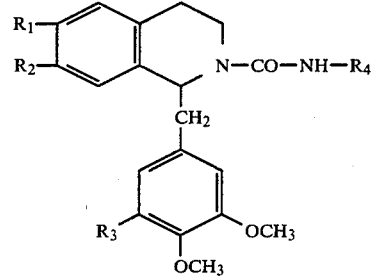

in which $R_1$ and $R_2$ are hydroxyl or methoxyl, $R_3$ is hydrogen or methoxy, $R_4$ is methyl or chloroethyl.

2. s-(+)-1-(3,4,5-trimethoxy-benzyl)-6,7-dihydroxy-2-[N-(2-chloroethyl)-carbamoyl]-1,2,3,4-tetrahydroisoquinoline as defined in claim 1.

3. s-(+)-1-(3,4,5-trimethoxybenzyl)-2-[N-methylcarbamoyl]-6,7-dihydroxy-1,2,3,4-tetrahydroisoquinoline as defined in claim 1.

4. 1-(3,4-dimethoxybenzyl)-2-[N-(chloroethyl)-carbamoyl]-6,7-dimethoxy-1,2,3,4-tetrahydroisoquinoline as defined in claim 1.

* * * * *